United States Patent [19]
Leffler et al.

[11] Patent Number: 5,569,369
[45] Date of Patent: Oct. 29, 1996

[54] CASSETTE FOR HIGH RESOLUTION GEL ELECTROPHORESIS

[75] Inventors: Charles E. Leffler, Brecksville; Gregory S. Bambeck, Kent, both of Ohio

[73] Assignee: Zaxis Inc., Hudson, Ohio

[21] Appl. No.: 488,844

[22] Filed: Jun. 9, 1995

[51] Int. Cl.[6] ............................. G01N 27/26; C25B 9/00
[52] U.S. Cl. .................... 204/620; 204/616; 204/617; 204/618; 204/619
[58] Field of Search ............................ 204/299 R, 182.8, 204/616, 617, 618, 619, 620

[56] References Cited

U.S. PATENT DOCUMENTS

| | | | |
|---|---|---|---|
| 4,707,233 | 11/1987 | Margolis | 204/182.3 |
| 4,772,373 | 8/1988 | Ebata et al. | 204/299 R |
| 4,909,918 | 3/1990 | Bambeck et al. | 204/299 R |
| 4,975,174 | 12/1990 | Bambeck et al. | 204/299 R |
| 5,284,565 | 2/1994 | Chu et al. | 204/299 R |

Primary Examiner—Kathryn Gorgos
Assistant Examiner—Alex Noguerola
Attorney, Agent, or Firm—Benesch, Friedlander, Coplan & Aronoff

[57] ABSTRACT

This invention is directed to a cassette for gel electrophoresis which may be easily disassembled without disrupting or damaging the gel and which prevents the gel from sliding out of the cassette. This invention is further directed to a cassette provided with a comb carrier which allows for the easy insertion of a comb into the cassette after the gel has been poured without damaging the gel and which protects the comb from having unwanted material enter into the comb and into the gel.

18 Claims, 6 Drawing Sheets

CASSETTE FOR HIGH RESOLUTION GEL ELECTROPHORESIS

FIELD OF INVENTION

This invention relates to electrophoresis apparatus and particularly to vertical electrophoresis devices and components therefor. More particularly, this invention relates to a novel cassette for high resolution gel electrophoresis. The novel cassette of the present invention may be easily assembled and disassembled, prevents the electrophoresis gel slab from slipping out of the cassette, and allows for a comb to be easily inserted into the interior of the cassette by the comb carrier which is fastened to the cassette.

BACKGROUND OF THE INVENTION

Electrophoresis involves the separation of charged molecular species in an electrical field. An electric field is applied to a macromolecular mixture, causing the mixture to be separated into fractions. Gel electrophoresis involves the migration of charged macromolecules through a porous gel under an applied electric field. Electrophoresis occurs because of differences in mobility of the different molecular species in the gel when subjected to electromotive force. Usually separation is based on differences in molecular weight, but can be based on differences in some other parameter, such as electrical charge.

Electrophoresis is a particularly desirable tool for separation or fractionation of macromolecular mixtures in which the molecular weight of the species present are from about 10,000 to about 1 million atomic mass units. Gel electrophoresis is a particularly suitable technique for fractionating protein mixtures, including DNA and RNA mixtures used in genetic studies. While electrophoresis has some limited use as a preparative tool, it is more widely used as an analytical tool.

Gel electrophoresis apparatus may be classified into two general types, vertical and horizontal. Both types have been extensively described in literature and patents. Vertical electrophoresis devices have an advantage in that cleaner separations and smoother flow of the macromolecular mixture to be fractionated are generally easier to attain in vertical apparatus than in horizontal apparatus due to greater electrical continuity between the electrodes and the gel.

U.S. Pat. No. 4,707,233 shows a representative vertical gel electrophoresis device. The apparatus shown therein comprises an open top container or tank having a basket-like gel cassette holder which is placed within the container or tank, a vertical gel cassette extending through the bottom wall of the gel cassette holder, a gasket forming a virtually fluid-tight joint between the gel cassette and the gel cassette holder, and oppositely charged electrodes on opposite sides of the non-conductive gel cassette holder walls so that electric current must pass through the gel matrix. The gel cassette is comprised of a pair of parallel plates joined together along their vertical edges by spacers, so that the gel cassette is open at the top and bottom but not along the sides, and a sample holder resembling a comb or a series of hollow tubes for directing macromolecular mixture through the gel matrix and thus between the walls of the cassette. The gel cassette may be held together by any suitable means, such as strips of vertically extending adhesive tape which overlay the outside surfaces of the spacer and the vertical sides of the plates, or the vertical plates may be fused together. The interior space of the gel cassette is filled with a suitable electrophoresis gel before the device is put into operation.

Various problems are associated with known gel cassettes. One problem involves the removal of the gel from the cassette for further processing after the electrophoresis run is completed. As conventional gel cassettes are often held together by strips of adhesive tape or by fusing the plates together, in order to remove the gel, the adhesive tape must be removed or the plates must be broken apart. The force required to disassemble the cassette by such methods can cause the plates to bend or otherwise interfere with the gel thereby disrupting or partially destroying the gel.

Another problem with the conventional gel cassettes, especially disposable gel cassettes, is that such cassettes are often comprised of a plastic material which may be very slippery. The slipperiness of the plastic material may result in part or all of the gel sliding out of the cassette during the electrophoresis run, thereby ruining the electrophoresis run.

An additional problem with conventional gel cassettes involves the combs used for directing macromolecular mixture through the gel cassette. In many conventional gel cassettes, the comb is inserted into the cassette prior to pouring the gel into the cassette. If a large number of electrophoresis runs are to be done wherein each run requires a different number of samples, cassettes having combs of differing numbers of sample wells must be kept on hand. Storing such large numbers of cassettes can be costly and cumbersome. Further, once the gel has been poured into the gel cassette, one is not able to change to a different comb having a differing number of sample wells.

Other prior art gel cassettes have attempted to overcome this problem by using combs which may be placed on top of the gel cassette after the gel is poured. The sample wells of the comb are in the shape of a shark tooth. The comb is placed at the top of the gel cassette in the opening between the two parallel plates, such that the pointed end of the shark tooth is placed into the gel. Samples of solutions to be fractionated are injected into the shark tooth shaped sample wells. The problem with these combs is that inserting the pointed end into the gel can damage the gel. Further, neither these gel cassettes nor the gel cassettes discussed above, wherein the comb is installed prior to the gel being poured, offer any protection to the top of the comb during the electrophoresis run. Dust or other undesirable particles may enter through the top of the sample wells and migrate into the gel disrupting or damaging the gel.

It is desirable to have a cassette for gel electrophoresis which may be easily disassembled without disrupting or damaging the gel and which prevents the gel from sliding out of the cassette. It is also desirable to have a cassette for gel electrophoresis which allows for the easy insertion of a comb into the cassette after the gel has been poured without damaging the gel and which protects the comb from having unwanted material enter into the comb and hence into the gel.

SUMMARY OF THE INVENTION

In accordance with the present invention, there is provided a cassette for gel electrophoresis which may be easily disassembled without disrupting or damaging the gel and which prevents the gel from sliding out of the cassette.

Further, in accordance with the present invention, there is provided a cassette for gel electrophoresis which allows for the easy insertion of a comb into the cassette after the gel has been poured without damaging the gel and which protects the comb from having unwanted material enter into the comb and into the gel.

Still further, in accordance with the present invention, there is provided a cassette comprised of:

a posterior plate having front and back surfaces, top and bottom edge surfaces, and side edge surfaces, wherein the front surface has a raised ridge located proximate to each of the side edge surfaces, each ridge including a plurality of keys spaced apart from each other and extending from the ridge in a direction opposite the side edge surface; and an anterior plate having front and back surfaces, top and bottom edge surfaces, side edge surfaces, and two opposing sidewalls adjacent the side edge surfaces, wherein the sidewalls have front and back surfaces and opposing inner and outer surfaces, and wherein the sidewalls have a plurality of keys spaced apart from each other extending perpendicularly from the inner surface in the direction of the opposite sidewall;

wherein the keys extending from the raised ridges of the posterior plate and the keys extending from the sidewalls of the anterior plate are removably mated, wherein the posterior plate and the anterior plate are fastened together in such a manner that the front surface of the posterior plate and the back surface of the anterior plate are adjacent each other and that the anterior plate and the posterior plate are generally parallel to each other, and wherein the raised ridges of the posterior plate extend to and are in contact with the back surface of the anterior plate providing a space between the anterior plate and the posterior plate for an electrophoresis gel.

Still further, in accordance with the present invention, there is provided a cassette for high resolution gel electrophoresis wherein the posterior plate is further comprised of a groove on the front surface of the posterior plate, wherein the groove is located near the bottom surface of the posterior plate, and wherein the groove prevents the electrophoresis gel from sliding out of the opening at the bottom of the cassette.

Still further, in accordance with the present invention, there is provided a comb carrier which is fastened to the cassette for holding and inserting a comb into the cassette which allows for the easy insertion of a comb into the cassette after the gel has been poured without damaging the gel and which protects the comb from having unwanted material enter into the comb and into the gel.

These and other aspects of the present invention will be apparent to one skilled in the art upon reading and understanding the specification which follows.

DETAILED DESCRIPTION OF THE PREFERRED EMBODIMENTS

Figure 1:
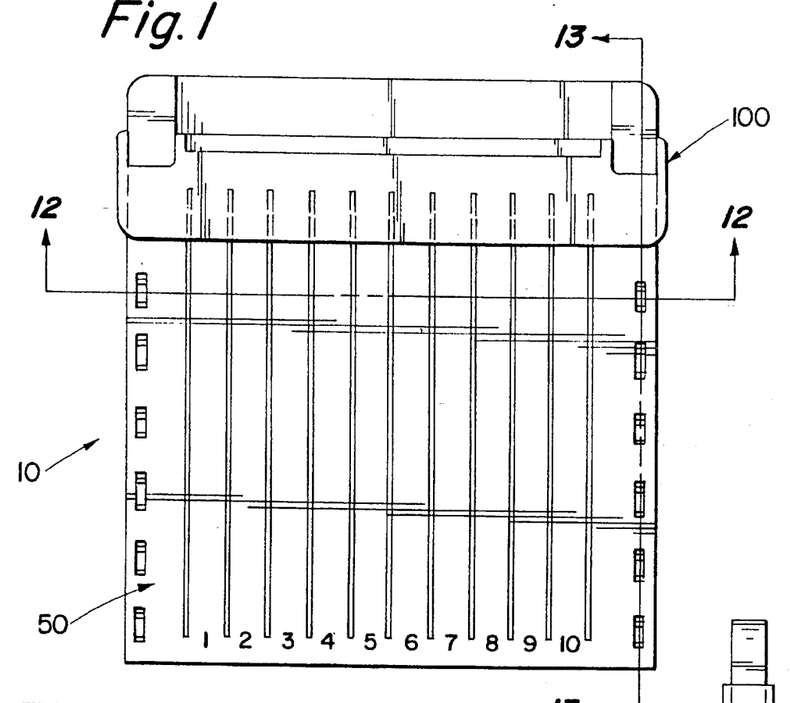
FIG. 1 is a front view of a cassette for gel electrophoresis with a comb carrier according to the present invention.
Figure 2:
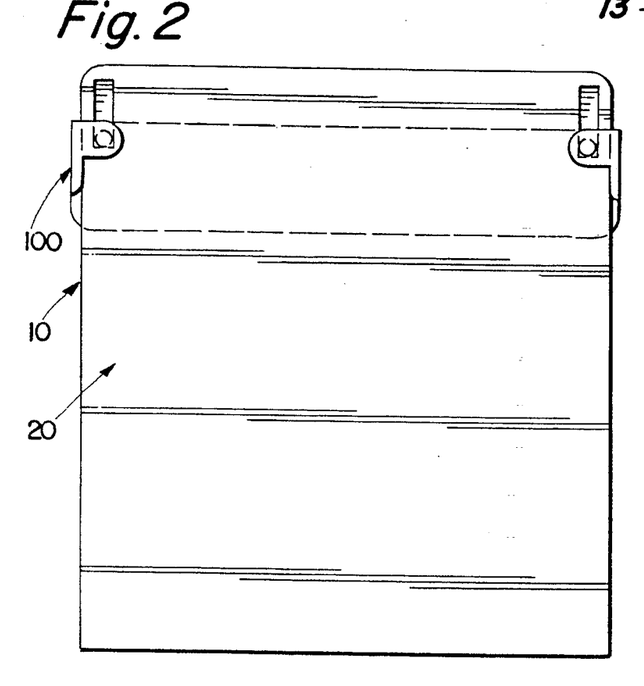
FIG. 2 is a rear view of a cassette for gel electrophoresis with a comb carrier according to the present invention.
Figure 3:
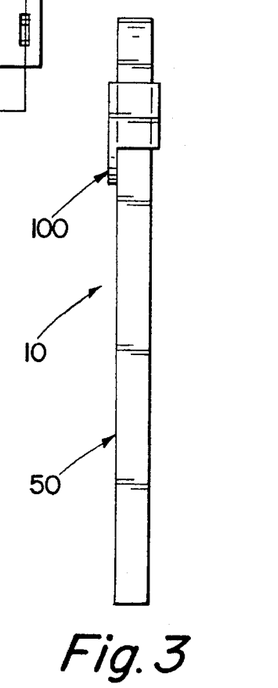
FIG. 3 is a side view of a cassette for gel electrophoresis with a comb carrier according to the present invention.
Figure 12:
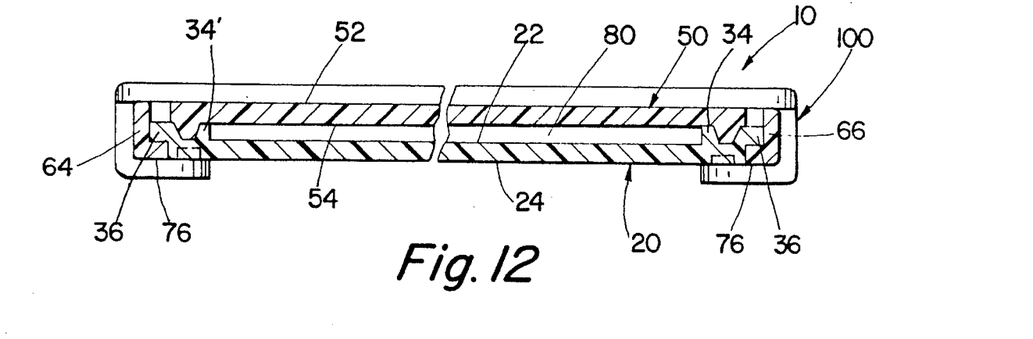
FIG. 12 is a horizontal cross-section of a cassette for gel electrophoresis taken on the line 12—12 of FIG. 1.
Figure 13:
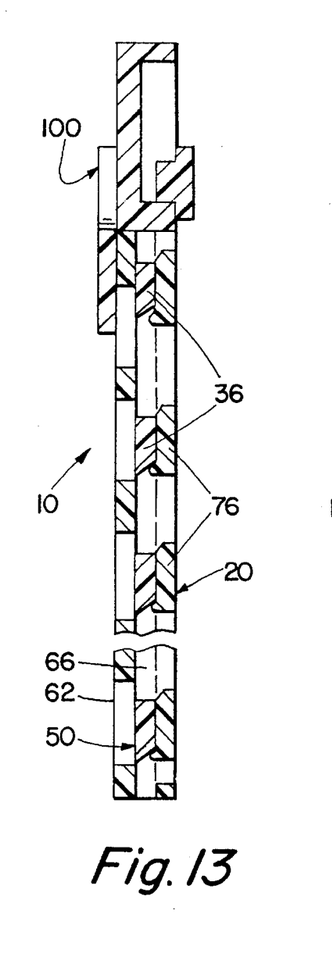
FIG. 13 is a vertical cross-section taken on the line 13—13 of FIG. 1.

Referring now to the drawings, wherein the showings are for the purposes of illustrating the preferred embodiments of the invention only and not for the purposes of limiting the scope of the claims, FIGS. 1, 2 and 3 show a cassette 10 for gel electrophoresis with a comb carrier 100 fastened to the cassette. The cassette is basically comprised of a posterior plate 20 and an anterior plate 50 wherein the posterior plate and the anterior plate are fastened together in such a manner that the posterior plate and the anterior plate are adjacent each other and generally parallel to each other. Further, the plates are fastened together in such a manner that a space 80 as shown in FIG. 12 is provided between the plates for the electrophoresis gel. The cassette is open at the top and bottom.

Figures 4, 5, 6:
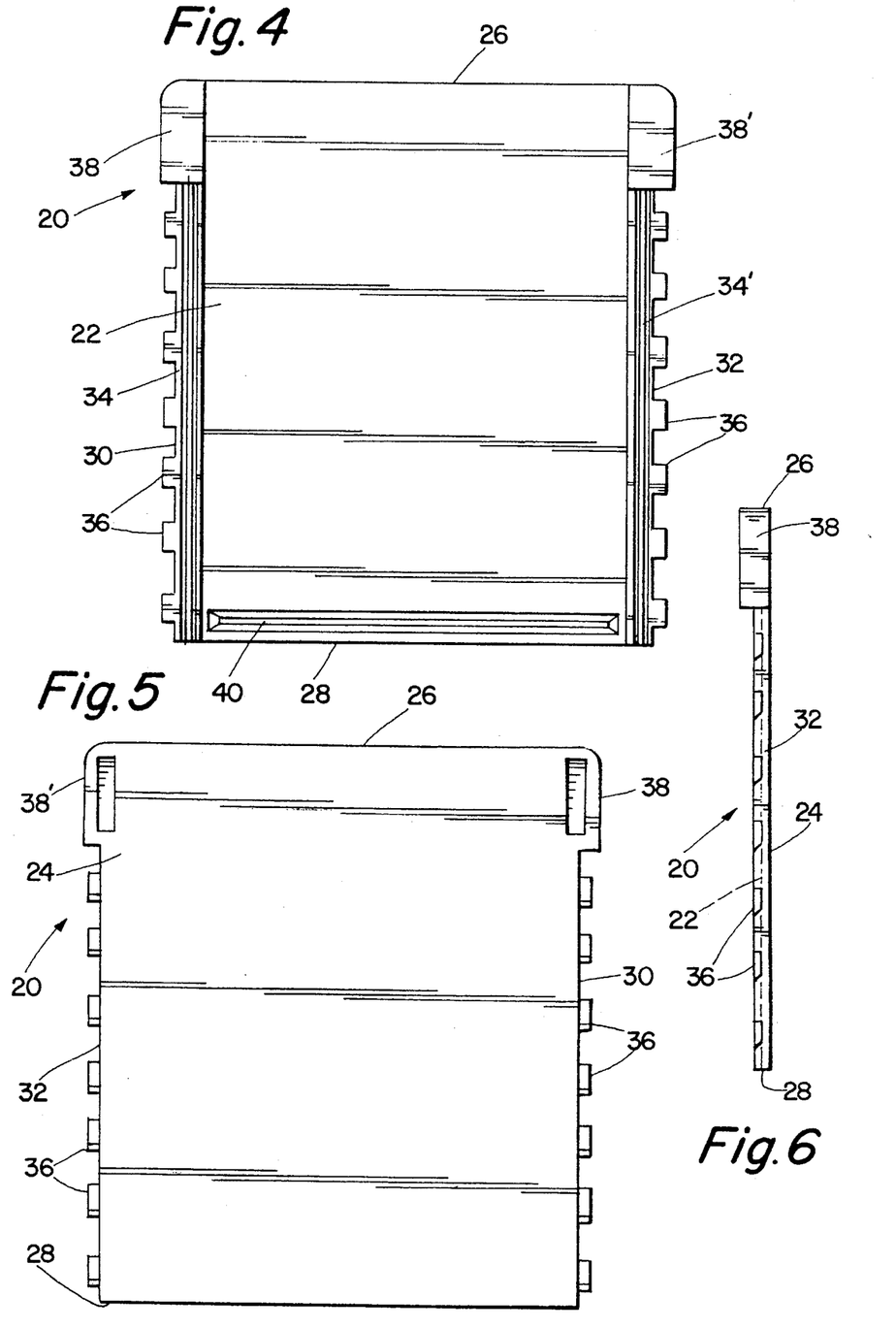
FIG. 4 is a front view of a posterior plate of a cassette for gel electrophoresis according to the present invention.
FIG. 5 is a rear view of a posterior plate of a cassette for gel electrophoresis according to the present invention.
FIG. 6 is a side view of a posterior plate of a cassette for gel electrophoresis according to the present invention.

The posterior plate 20 as shown in FIGS. 4, 5 and 6 is comprised of opposing front surface 22 and back surface 24, opposing top edge surface 26 and bottom edge surface 28, and opposing side edge surfaces 30 and 32 wherein one of the side edge surfaces 32 is shown in FIG. 6. The front surface 22 has raised ridge 34 and 34' located proximate to each of the side edge surfaces 30 and 32, respectively. The ridges 34 and 34' extend across a portion of the front surface 22 generally parallel to the side edge surfaces 30 and 32, respectively. The ridges 34 and 34' include a plurality of keys 36 spaced apart from each other and extending outwardly from the ridges 34 and 34' in a direction perpendicular to the side edge surface. The posterior plate has a length greater than the length of the anterior plate. A portion of the posterior plate 20 extends above the top surface of the anterior plate 50 when the plates are assembled. The front surface of the portion of the posterior plate 20 which extends above the anterior plate 50 has raised portions 38 and 38' located proximate to each of the side edge surfaces 30 and 32, respectively, of the posterior plate.

The posterior plate 20 may further have a groove 40 on the front surface 22 of the posterior plate. The groove 40 is located near the bottom edge surface 28 of the posterior plate and extends across a portion of the front surface 22 generally parallel to the bottom edge surface. The groove 40 prevents the electrophoresis gel from sliding out of the opening at the bottom of the cassette.

Figure 7:
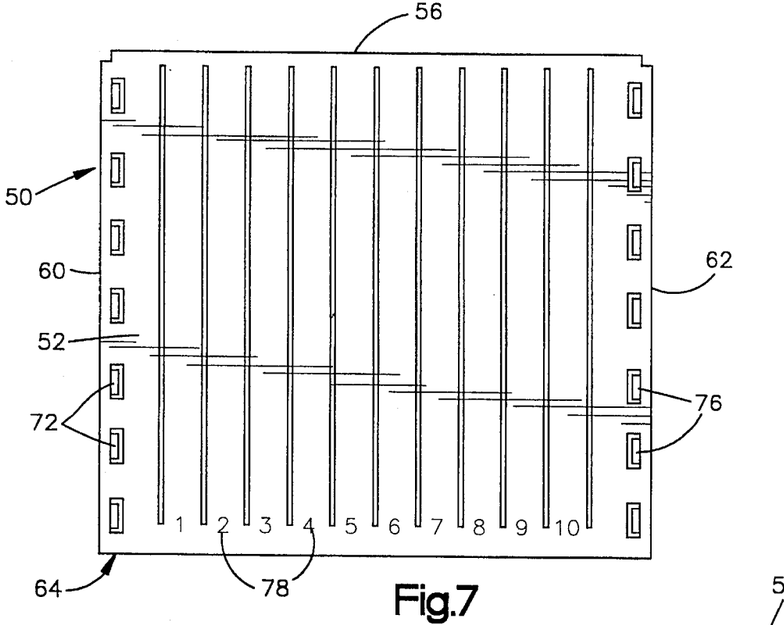
FIG. 7 is a front view of an anterior plate of a cassette for gel electrophoresis according to the present invention.
Figure 8:
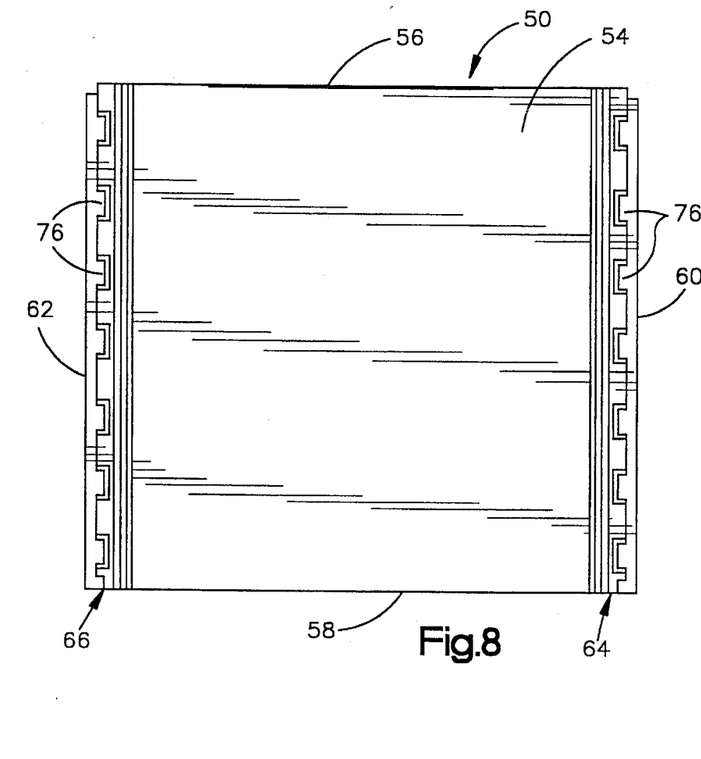
FIG. 8 is a rear view of an anterior plate of a cassette for gel electrophoresis according to the present invention.
Figure 9:
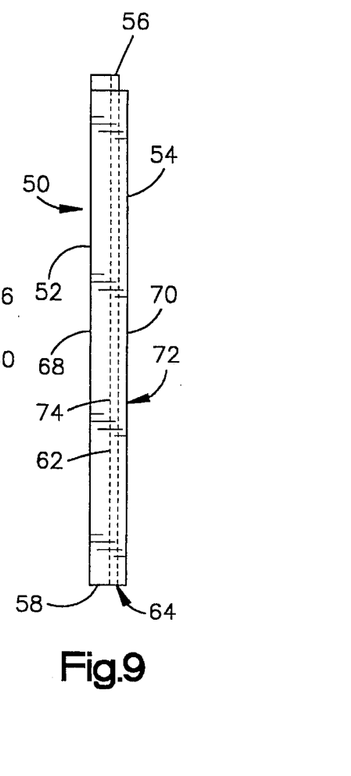
FIG. 9 is a side view of an anterior plate of a cassette for gel electrophoresis according to the present invention.
Figure 10:
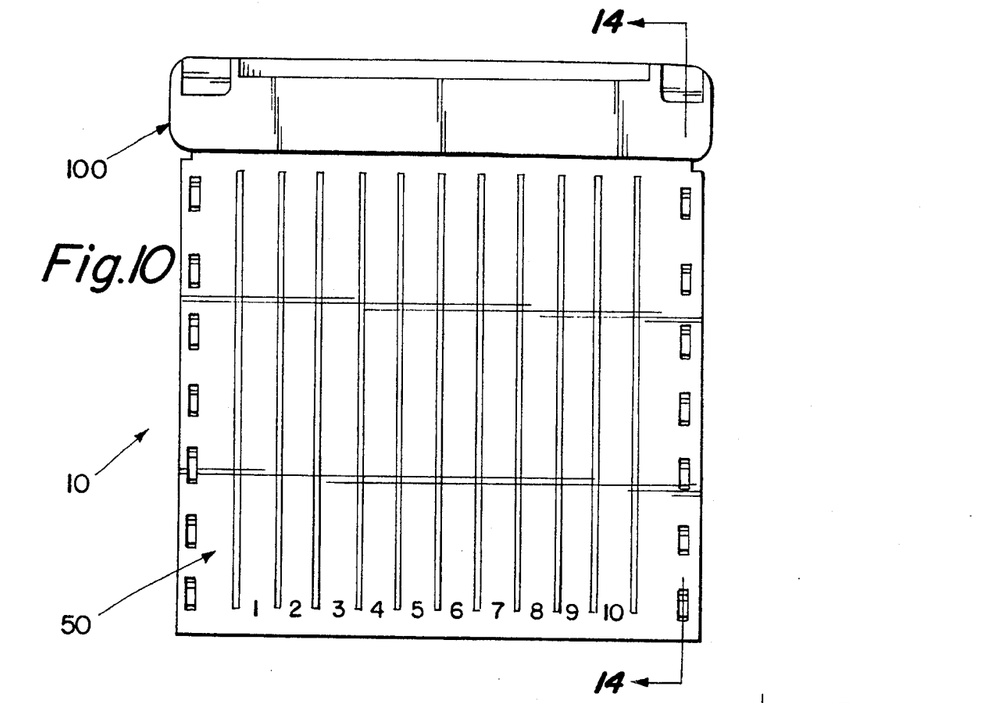
FIG. 10 is a front view of a cassette for gel electrophoresis with its comb carrier in raised position prior to removal of anterior plate according to the present invention.
Figure 11:
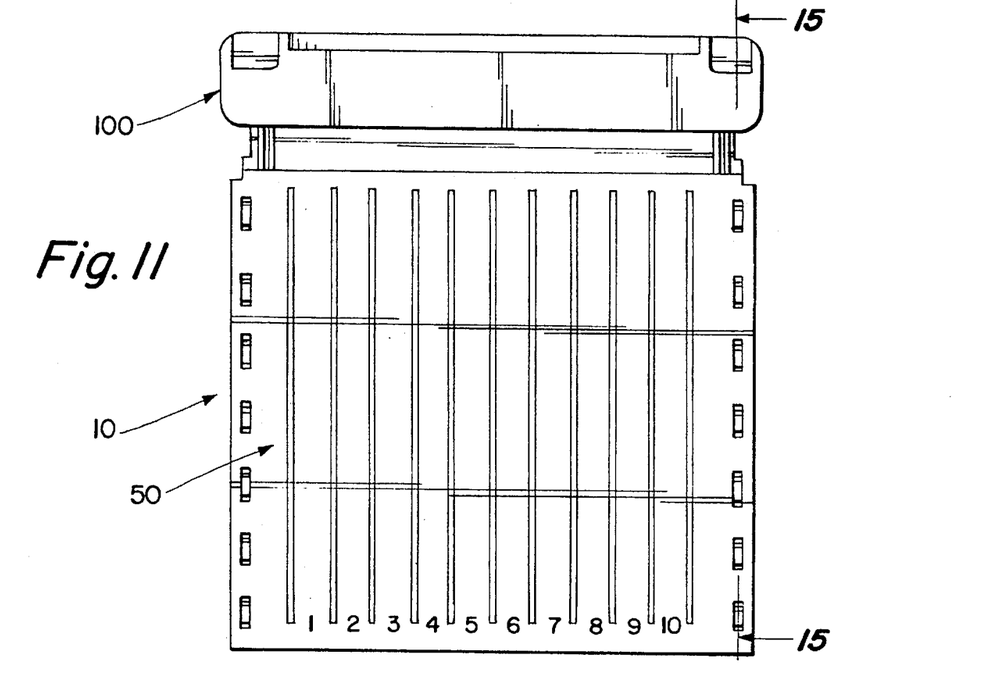
FIG. 11 is a front view of a cassette for gel electrophoresis with its comb carrier in raised position and anterior plate in lowered position prior to removal of anterior plate according to the present invention.

The anterior plate 50 as shown in FIGS. 7, 8 and 9 is comprised of opposing front surface 52 and back surface 54, opposing top edge surface 56 and bottom edge surface 58, opposing side edge surfaces 60 and 62, and two opposing sidewalls 64 and 66. The sidewalls 64 and 66 extend from the side edge surfaces outwardly in a direction perpendicular to and opposite the back surface 54. One of the sidewalls 64 is shown in FIG. 9. The sidewalls 64 and 66 have opposing front surface 68 and back surface 70, and opposing inner surface 72 and outer surface 74. The sidewalls 64 and 66 have a plurality of keys 76 spaced apart from each other. The keys 76 extend perpendicularly from the inner surface of the sidewalls in the direction of the opposite sidewall. The keys 76 are located near the back surface of the sidewalls at a predetermined distance from the back surface 54 of the anterior plate 50 providing a space between the keys 76 extending from the sidewalls 64 and 66 and the back surface 54 of the anterior plate. The predetermined distance is equal to the height of the keys extending from the raised ridges of the posterior plate.

The anterior plate has a shape similar to the shape of the posterior plate, except that the anterior plate is wider than the posterior plate. The width of the anterior plate is equal to the width of the posterior plate plus the width of the keys extending from each of the raised ridges on the posterior plate.

The front surface of the anterior plate may include parallel lines extending across a portion of the front surface parallel to the side edge surfaces. The lines are spaced apart a predetermined distance and are used for marking the different lanes of material fractionated.

The back surface of the anterior plate may be comprised of reference numerals 78 located near the bottom surface of the anterior plate. The numerals extend across the back surface of the anterior plate and since a preferred material of construction is transparent plastic, the numerals may be viewed from the front surface of the anterior plate. The reference numerals are in contact with the gel and imprint the number into the gel. The numbers imprinted on the gel provide easy reference to the samples of material fractionated.

Referring to FIGS. 10–13, when the cassette is assembled, the keys 36 extending from the raised ridges 34 and 34' of the posterior plate 20 fit within the space between the keys 76 extending from the sidewalls 64 and 66 and the bottom surface 54 of the anterior plate 50 interconnecting the posterior plate with the anterior plate and fastening the posterior plate to the anterior plate. When the plates are assembled, the keys 36 extending from the raised ridges 34 and 34' of the posterior plate are in contact with the keys 76 extending from the side walls 64 and 66 and the bottom surface 54 of the anterior plate. This contact between the keys 36, keys 76 and the back surface of the anterior plate help to maintain a fixed relative positioning of the plates. The posterior plate 20 and the anterior plate 50 are fastened together in such a manner that the front surface 22 of the posterior plate 20 and the back surface 54 of the anterior plate 50 are adjacent each other and the anterior plate and the posterior plate are generally parallel or coplanar with each other. The raised ridges 34 and 34' of the posterior plate extend to and are in contact with the back surface 54 of the anterior plate providing a space between the anterior plate and the posterior plate for an electrophoresis gel. The cassette 10 has an interior 80 which is defined by the space between the anterior and posterior plates and the raised ridges 34 of the posterior plate. The cassette is open at the top and bottom surfaces of the anterior and posterior plates.

Figure 14:
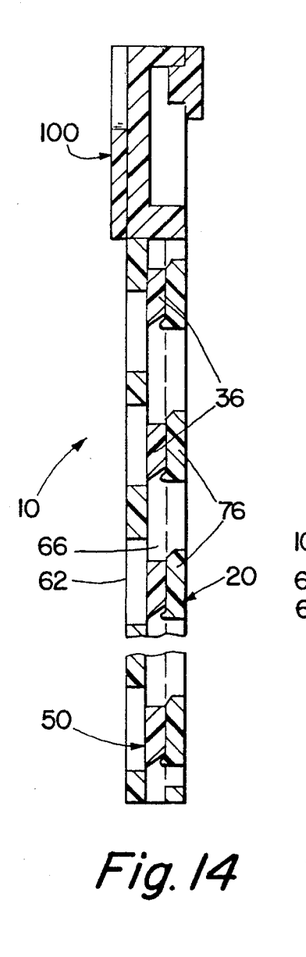
FIG. 14 is a vertical cross-section taken on the line 14—14 of FIG. 10.
Figure 15:
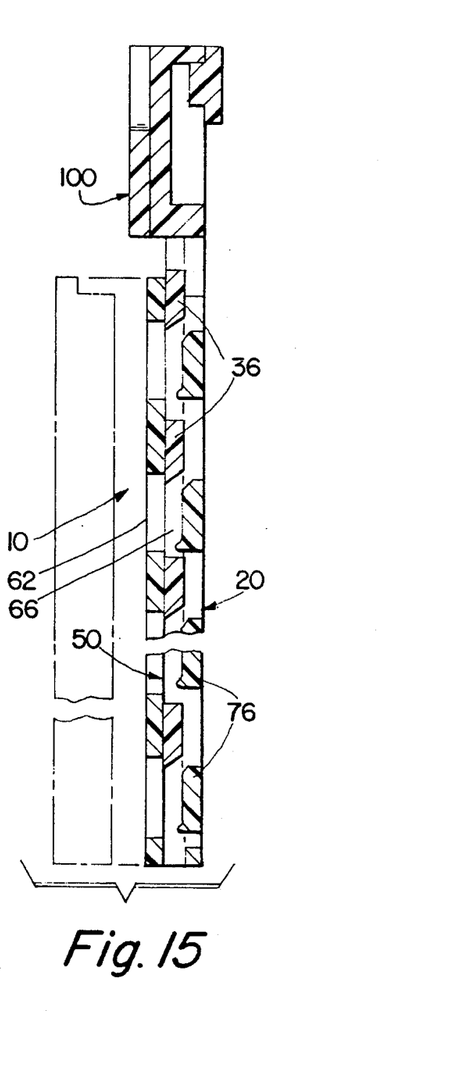
FIG. 15 is a vertical cross-section taken on the line 15—15 of FIG. 11.

The cassette of the present invention may be disassembled easily in order to remove the electrophoresis gel from the cassette without disrupting or damaging the electrophoresis. The cassette is disassembled as shown in FIGS. 14 and 15 by applying pressure to the top of the anterior plate 50 in the direction of the bottom of the anterior plate, the side edge surfaces 60 and 62, and the sidewalls 64 and 66 (wherein only one of the side edge surfaces 62 and one of the side walls 66 is shown). Applying force to the top, side edge surfaces, and sidewalls causes the anterior plate to move in the direction of the bottom of the cassette wherein the keys 36 extending from the raised ridges (not shown in this drawing) of the posterior plate 20 and the keys 76 extending from the sidewalls of the anterior plate 50 are no longer in contact with one another whereby the anterior plate may be removed from the posterior plate.

The cassette may be comprised of any suitable material, such as glass or plastic. Preferably, the cassette is comprised of plastic or other disposable material. More preferably, the cassette is comprised of a transparent plastic material.

The interior of the cassette is filled with an electrophoresis gel. Any of the electrophoresis gels known in the art may be used. For instance, a polyacrylamide gel, which may be cross-linked with a small amount of cross-linking agent, for example, bis-acrylamide, and having a gradient concentration, wherein the gel is more concentrated at the bottom of the cassette than at the top, may be used for separation of macromolecular species and particularly proteins wherein the minimum molecular weight present is about 10,000 or higher such as disclosed in U.S. Pat. No. 4,909,918.

The gel is preferably prepared in precast form, having a width and thickness equal to those of the interior of the cassette and a height slightly less than that of the cassette. The gel is inserted into the interior of the cassette by means known in the art, prior to assembly of the electrophoresis device. The gel should be charged to the cassette so that the bottom edge of the gel coincides with the bottom edge of the cassette. The gel may be loaded into the cassette to any level desired by the user such as disclosed in U.S. Pat. No. 4,975,174.

After the gel is inserted into the cassette, a comb (not shown) having a plurality of dividers forming side by side sample wells is inserted into the top of the cassette such as disclosed in U.S. Pat. No. 4,909,918. Preferably, the comb is formed from a thin rectangular sheet of plastic material. The comb has a plurality of spaced hollow parallel ridges and a plurality of spaced parallel coplanar flat portions therebetween. The ridges and flat portions extend between opposite sides of the sheet. The ridges have convex central portions and are substantially uniform height as measured from the plane of the flat portions. The comb is adapted to be inserted into the cassette such that the flat portions are in frictional engagement with the posterior and the ridges are in frictional engagement with the anterior plate, whereby the comb and the plates form a plurality of parallel sample wells for gel and material to be fractionated in alternating relationship with the parallel channels for gel alone.

Figure 16:
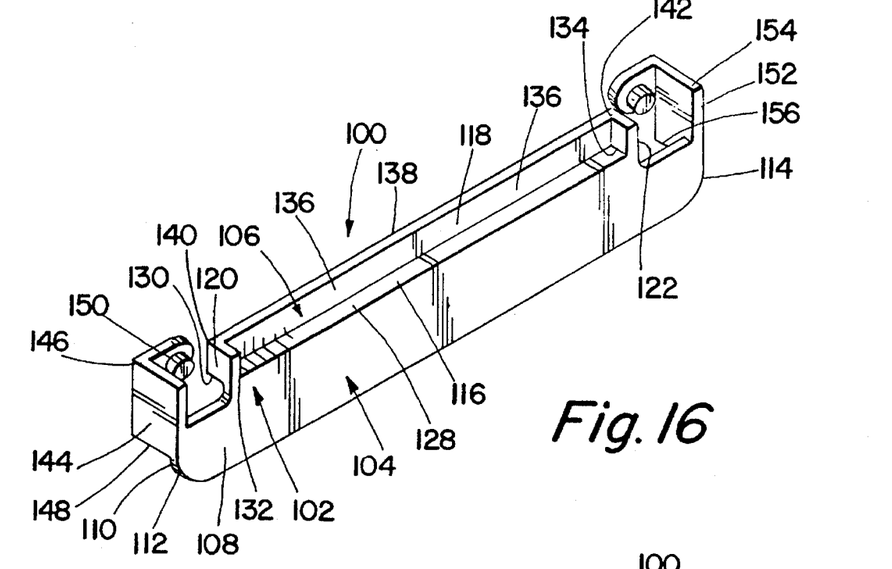
FIG. 16 is a perspective view of a comb carrier for a cassette for gel electrophoresis according to the present invention.
Figure 17:
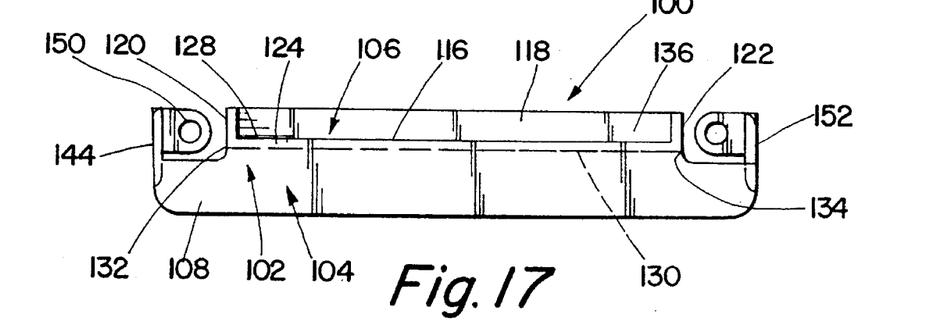
FIG. 17 is a front view of a comb carrier for a cassette for gel electrophoresis according to the present invention.
Figure 18:
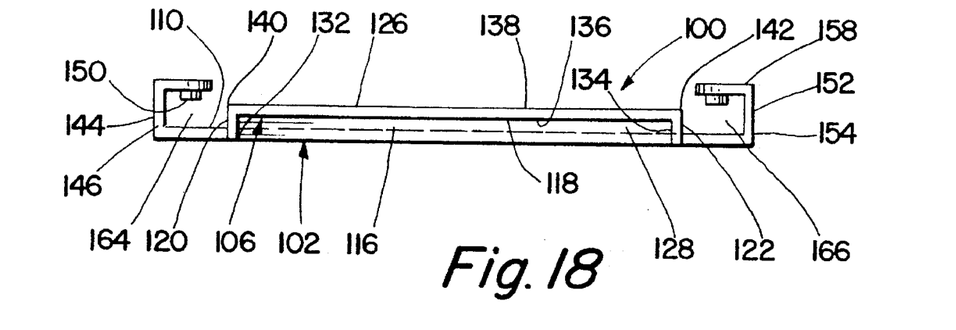
FIG. 18 is a top plan view of a comb carrier for a cassette for gel electrophoresis according to the present invention.

A comb is inserted into the cassette with a comb carrier 100 as shown in FIGS. 16–18. The comb carrier is comprised of a front member 102 having a lower portion 104 and an upper portion 106. The lower portion has a front surface 108, a back surface 110, and two opposing side surfaces 112, 114. The upper portion 106 has a bottom section 116, a back section 118, a first side section 120, and a second side section 122. The bottom section 116 has a front surface 124, a back surface 126, a top surface 128, a bottom surface 130, and two opposing side surfaces 132, 134. The bottom section extends perpendicularly from the back surface 110 of the lower portion. The back section 118 has a front surface 136, a back surface 138, and two opposing side surfaces 140, 142. The back section extends perpendicularly upwardly from the back surface 126 of the bottom section. The first side section 120 extends perpendicularly upwardly from side surface 132 of the bottom section 116, and further extends perpendicularly from side surface 140 of the back section 118. The second side section 122 extends perpendicularly upwardly from side surface 134 of the bottom section, and further extends perpendicularly from side surface 142 of the back section 118.

The comb carrier is further comprised of a first side member 144 extending perpendicularly from side surface 112 of the lower portion 104 of the front member 102 in a direction away from the back surface 110 of the lower portion. The side member has a top surface 146 and a bottom surface 148 and further has a tab 150 extending perpendicularly in a direction towards the opposite side surface of the lower portion. The comb carrier further has a second side member 152 extending perpendicularly from side surface 114 of the lower portion 104 of the front member 102 in a direction away from the back surface 110 of the lower portion. The side member has a top surface 154 and a bottom surface 156 and further has a tab 158 extending perpendicularly in a direction towards the opposite side surface of the lower portion.

The first side member 144, the first side section 120 of the upper portion 106 of the front member 102, and a portion of the lower portion 104 nearest the first side member define a first opening 164. The second side member 152, the second side section 122 of the upper portion 106 of the front member, and a portion of the lower portion 104 nearest the second side member define a second opening 166. The raised portions 38 and 38' on the front surface 22 of the posterior plate 20 are inserted into said openings fastening the carrier to the cassette.

The comb carrier may be comprised of any suitable material. Preferably, the comb is comprised of plastic.

The comb is inserted in the interior of said cassette by placing the comb on the portion of the posterior plate which extends above the top surface of the anterior plate when the plates are assembled. The comb carrier is placed over the comb and fastened to the cassette whereby the comb is in contact with the back surface 110 of the lower portion 104 and the bottom surface 130 of the bottom section 116 of the upper portion 106 of the front member 102. Pressure is applied to the top of the side members of the carrier in the direction of the bottom of the cassette thereby moving the carrier down the raised portions on the front surface of the posterior plate in the direction of the bottom of the cassette. The comb which is in contact with the back surface 110 of the lower portion 104 and the bottom surface 130 of the bottom section 116 of the upper portion 106 of the front member 102 is forced into the interior of the cassette.

The comb may be stored in the comb carrier on the portion of the posterior plate which extends above the top surface of the anterior plate when the plates are assembled until such time as the comb is to be inserted into the cassette.

The comb carrier of the present invention has several advantages, such as the comb carrier allows the comb to be stored with the cassette and then easily inserted into the cassette after the gel has been poured into the cassette without disrupting or damaging the gel. Another advantage is that one is able to change to a different comb having a differing number of sample wells even after the gel has been poured into the cassette and set. In addition, further, the user does not need to keep a large number of cassettes on hand having combs having differing numbers of sample wells. Further, if the user desires to run an electrophoresis with a differing number of samples than the comb which is included with the cassette, the user may simply use a different comb with the cassette. The comb carrier further functions to protect the comb and the gel from unwanted materials entering into the sample wells and into the gel. The comb carrier covers the top of the comb preventing such materials from entering through the sample wells.

The cassette for gel electrophoresis of the present invention may be easily disassembled without disrupting or damaging the gel. In addition, the cassette of the present invention prevents the gel from sliding out of the cassette. Further, the cassette is provided with a comb carrier which allows for the easy insertion of a comb into the cassette after the gel has been poured without damaging the gel and which protects the comb from having unwanted material enter into the comb and into the gel.

Although various exemplary embodiments of the invention have been disclosed for illustrative purposes, it is understood that variations and modifications can be made by one skilled in the art without departing from the spirit or scope of the invention.

What is claimed is:

1. A cassette for high resolution gel electrophoresis, said cassette comprising:

a posterior plate having opposing front and back surfaces, opposing top and bottom edge surfaces, and opposing side edge surfaces, wherein said front surface has a raised ridge located proximate to each of said side edge surfaces and extending across a portion of said front surface generally parallel to said side edge surfaces, each ridge including a plurality of keys spaced apart from each other and extending from said ridge in a direction opposite said proximate side edge surface; and an anterior plate shaped similarly to said posterior plate having opposing front and back surfaces, opposing top and bottom edge surfaces, opposing side edge surfaces, and two opposing sidewalls adjacent to said side edge surfaces, wherein said sidewalls have front and back surfaces, and opposing inner and outer surfaces, and wherein said sidewalls have a plurality of keys spaced apart from each other extending perpendicularly from said inner surface of said sidewalls in the direction of the opposite sidewall, wherein said anterior plate has a shape similar to said posterior plate;

wherein the keys extending from the raised ridges of said posterior plate fit within the space between the keys extending from the sidewalls and the back surface of said anterior plate interconnecting said posterior plate with said anterior plate and fastening said posterior plate to said anterior plate, wherein said posterior plate and said anterior plate are fastened together in such a manner that the front surface of said posterior plate and the back surface of said anterior plate are adjacent each other and said anterior plate and said posterior plate are generally parallel to each other, and wherein said raised ridges of said posterior plate extend to and are in contact with the back surface of said anterior plate providing a space between said anterior plate and said posterior plate for an electrophoresis gel;

wherein said cassette has an interior which is defined by the space between said anterior and posterior plates and the raised ridges of said posterior plate, and wherein said cassette is open at the top and bottom surfaces of said anterior and posterior plates.

2. The cassette of claim 1 wherein the keys extending from the sidewalls of the anterior plate are located proximate to the back surface of the sidewalls a distance from the back surface of the anterior plate approximately equal to a height of the keys extending from the raised ridges of the posterior plate providing a space between the keys extending from the sidewalls and the back surface of the anterior plate.

3. The cassette of claim 2 wherein the anterior plate has a width equal to the width of the posterior plate plus a width of the keys extending from each of said raised ridges on the posterior plate.

4. The cassette of claim 3 in which said keys are removably mated such that the keys on the posterior plate fit within the space between the keys on the anterior plate and the back surface of the anterior plate thereby interconnecting the posterior plate and the anterior plate so as to fasten them together.

5. The cassette of claim 1 which includes a groove on the front surface of said posterior plate located proximate to the bottom edge surface of said posterior plate and extending across a portion of said front surface generally parallel to said bottom edge surface.

6. The cassette of claim 1 further including a plurality of spaced apart parallel lines affixed across a portion of the front surface of the anterior plate, said lines running generally parallel to the side edge surfaces.

7. The cassette of claim 1 wherein the posterior plate is longer than the anterior plate and such that a portion of the posterior plate extends above the top edge surface of the anterior plate when said plates are assembled, further including a raised portion on the front surface of said portion located proximate to each of the side edge surfaces of said posterior plate.

8. The cassette of claim 7, further including a comb carrier comprising:

a front member having a lower portion and an upper portion; said lower portion having a front surface, a back surface, and two opposing side surfaces, said upper portion having a bottom section, a back section, a first side section, and a second side section; said bottom section having a front surface, a back surface, a top surface, a bottom surface and two opposing side surfaces and extending generally perpendicularly from the back surface of said lower portion; said back section having a front surface, a back surface, and two opposing side surfaces extending perpendicularly upwardly from the back surface of said bottom section; the first side section extending perpendicularly upwardly from one of the side surfaces of said bottom section, and further extending generally perpendicularly from one of the side surfaces of said back section; and the second side section extending perpendicularly upwardly from the other side surface of said bottom section, and further extending generally perpendicularly from the other side surface of said back section;

a first side member extending perpendicularly from one of the side surfaces of the lower portion of said front member in a direction away from the back surface of the lower portion, said side member having a top and a bottom and having a tab extending perpendicularly in a direction towards the opposite side surface of said lower portion; and a second side member extending perpendicularly from one of the side surfaces of the lower portion of said front member in a direction away from the back surface of the lower portion, said side member having a top and a bottom and having a tab extending perpendicularly in a direction towards the opposite side surface of said lower portion;

wherein the first side member, the first side section of the upper portion of said front member, and a portion of the lower portion nearest the first side member define a first opening, and wherein the second side member, the second side section of the upper portion of said front member, and a portion of the lower portion nearest the second side member define a second opening, whereby the raised portions on the front surface of said posterior plate are inserted into said openings fastening said carrier to said cassette.

9. The cassette of claim 1 wherein said cassette is comprised of a plastic material.

10. A cassette for high resolution gel electrophoresis, said cassette comprising:

a posterior plate having opposing front and back surfaces, opposing top and bottom edge surfaces, and opposing side edge surfaces, wherein said front surfaces has a raised ridge located proximate to each of said side surfaces and extending across a portion of said front surface generally parallel to said side surfaces, each ridge having a plurality of keys spaced apart from each other and extending generally perpendicularly from said ridge in a direction opposite said proximate side edge surface; and an anterior plate shaped similarly to said posterior plate having opposing front and back surfaces, opposing top and bottom edge surfaces, opposing side edge surfaces, and two opposing sidewalls extending from the side edge surfaces outwardly in a direction perpendicular to and opposite the back surface, wherein said sidewalls have front and back surfaces and opposing inner and outer surfaces, and wherein said sidewalls have a plurality of keys spaced apart from each other extending perpendicularly from said inner surface of said sidewalls in the direction of the opposite sidewall, wherein said keys are located proximate to the back surface of the sidewalls a distance from the back surface of the anterior plate approximately equal to a height of the keys extending from the raised ridges of the posterior plate providing a space between the keys extending from the sidewalls and the back surface of the anterior plate, wherein said anterior plate has a width equal to the width of said posterior plate plus a width of the keys extending from each of said raised ridges on said posterior plate;

wherein the keys extending from the raised ridges of said posterior plate fit within the space between the keys extending from said sidewalls and the back surface of said anterior plate interconnecting said posterior plate with said anterior plate and fastening said posterior plate to said anterior plate, wherein said posterior plate and said anterior plate are fastened together in such a manner that the front surface of said posterior plate and the back surface of said anterior plate are adjacent each other and said anterior plate and said posterior plate are generally parallel to each other, and wherein said raised ridges of said posterior plate extend to and are in contact with the back surface of said anterior plate providing a space between said anterior plate and said posterior plate for an electrophoresis gel;

wherein said cassette has an interior which is defined by the space between said anterior and posterior plates and the raised ridges of said posterior plate, and wherein said cassette is open at the top and bottom surfaces of said anterior and posterior plates.

11. The cassette of claim 10 wherein said cassette may be disassembled in order to remove electrophoresis gel from the cassette by applying pressure to the top and side surfaces of said anterior plate in the direction of the bottom surface of said anterior plate, whereby the keys extending from the raised ridges of said posterior plate and the keys extending from the sidewalls are no longer in contact with one another so that said anterior plate may be removed from said posterior plate.

12. The cassette of claim 10 which includes a groove on the front surface of said posterior plate located proximate to the bottom edge surface of said posterior plate and extending across a portion of said front surface generally parallel to said bottom edge surface.

13. The cassette of claim 10 further including a plurality of spaced apart parallel lines affixed across a portion of the front surface of the anterior plate, said lines running generally parallel to the side edge surfaces.

14. The cassette of claim 10 wherein the posterior plate is longer than the anterior plate and such that a portion of the posterior plate extends above the top edge surface of the anterior plate when said plates are assembled, further including a raised portion on the front surface of said portion located proximate to each of the side edge surfaces of said posterior plate.

15. The cassette of claim 14, further including a comb carrier comprising:

a front member having a lower portion and an upper portion; said lower portion having a front surface, a back surface, and two opposing side surfaces, said upper portion having a bottom section, a back section, a first side section, and a second side section; said bottom section having a front surface, a back surface, a top surface, a bottom surface and two opposing side surfaces and extending generally perpendicularly from the back surface of said lower portion; said back section having a front surface, a back surface, and two opposing side surfaces extending perpendicularly upwardly from the back surface of said bottom section; the first side section extending perpendicularly upwardly from one of the side surfaces of said bottom section, and further extending generally perpendicularly from one of the side surfaces of said back section; and the second side section extending perpendicularly upwardly from the other side surface of said bottom section, and further extending generally perpendicularly from the other side surface of said back section;

a first side member extending perpendicularly from one of the side surfaces of the lower portion of said front member in a direction away from the back surface of the lower portion, said side member having a top and a bottom and having a tab extending perpendicularly in a direction towards the opposite side surface of said lower portion; and a second side member extending perpendicularly from one of the side surfaces of the lower portion of said front member in a direction away from the back surface of the lower portion, said side member having a top and a bottom and having a tab extending perpendicularly in a direction towards the opposite side surface of said lower portion;

wherein the first side member, the first side section of the upper portion of said front member, and a portion of the lower portion nearest the first side member define a first opening, and wherein the second side member, the second side section of the upper portion of said front member, and a portion of the lower portion nearest the second side member define a second opening, whereby the raised portions on the front surface of said posterior plate are inserted into said openings fastening said carrier to said cassette.

16. The cassette of claim 15 in which the comb may be inserted in the interior of said cassette, including a comb placed on the portion of said posterior plate extending above the top surface of said anterior plate when said plates are assembled;

a carrier fastened to said cassette whereby said comb is in contact with the back surface of the lower portion and the bottom surface of the bottom section of the upper portion of the front member; and side members of said carrier to which pressure is applied in the direction of the bottom of the cassette thereby moving the carrier down the raised portions on the front surface of said posterior plate in the direction of the bottom of said cassette, whereby said comb which is in contact with the back surface of the lower portion and the bottom surface of the bottom section of the upper portion of the front member is forced into the interior of said cassette.

17. The cassette of claim 16 wherein said comb carrier is comprised of a plastic material.

18. The cassette of claim 10 wherein said cassette is comprised of a plastic material.

* * * * *